(12) United States Patent
Shano

(10) Patent No.: US 8,475,457 B2
(45) Date of Patent: Jul. 2, 2013

(54) CLIP-LIKE IMPLANT FOR OSTEOSYNTHESIS

(76) Inventor: Majid Shano, Waldmunchen (DE)

(*) Notice: Subject to any disclaimer, the term of this patent is extended or adjusted under 35 U.S.C. 154(b) by 509 days.

(21) Appl. No.: 12/223,713

(22) PCT Filed: Jan. 31, 2007

(86) PCT No.: PCT/DE2007/000162
§ 371 (c)(1),
(2), (4) Date: Aug. 7, 2008

(87) PCT Pub. No.: WO2007/093147
PCT Pub. Date: Aug. 23, 2007

(65) Prior Publication Data
US 2009/0062800 A1   Mar. 5, 2009

(30) Foreign Application Priority Data

Feb. 11, 2006   (DE) .......................... 10 2006 006 315
Feb. 11, 2006   (DE) .................... 20 2006 002 182 U
Oct. 27, 2006   (DE) .................... 20 2006 016 492 U

(51) Int. Cl.
*A61B 17/064*   (2006.01)
*A61B 17/03*   (2006.01)

(52) U.S. Cl.
USPC .............................. 606/75; 606/219; 411/476

(58) Field of Classification Search
USPC ........................... 606/75, 213–227, 300–331;
227/175.1–175.4, 176.1, 177.1, 178.1, 179.1,
227/180.1, 181.1, 182.1; 411/475–476, 920
See application file for complete search history.

(56) References Cited

U.S. PATENT DOCUMENTS

| RE23,566 | E  | * | 10/1952 | Henriksen ..................... 411/476 |
| 5,053,038 | A  |   | 10/1991 | Sheehan |
| 5,147,381 | A  | * | 9/1992  | Heimerl et al. ............... 606/219 |
| 5,167,665 | A  |   | 12/1992 | McKinney |
| 5,246,443 | A  | * | 9/1993  | Mai ................................ 606/78 |
| 5,314,160 | A  | * | 5/1994  | Larsen .......................... 248/547 |
| 5,474,557 | A  | * | 12/1995 | Mai ................................ 606/78 |
| 5,658,312 | A  | * | 8/1997  | Green et al. .................. 606/219 |
| 6,325,805 | B1 | * | 12/2001 | Ogilvie et al. ................. 606/75 |
| 6,776,784 | B2 | * | 8/2004  | Ginn ............................ 606/151 |
| 2002/0029044 | A1 |   | 3/2002  | Monassevitch |
| 2003/0139746 | A1 |   | 7/2003  | Groiso |
| 2005/0096660 | A1 | * | 5/2005  | Allen ............................. 606/75 |
| 2005/0267530 | A1 | * | 12/2005 | Cummins ..................... 606/219 |

FOREIGN PATENT DOCUMENTS

| DE | 3115207 | 4/1982 |
| DE | 3212828 | 11/1982 |
| EP | 130784  | 1/1997 |

(Continued)

*Primary Examiner* — Kevin T Truong
*Assistant Examiner* — Larry E. Waggle, Jr.
(74) *Attorney, Agent, or Firm* — Welsh Flaxman & Gitler LLC

(57) ABSTRACT

The invention relates to a clip-like implant for osteosynthesis of at least two repositioned bone fragments, with at least two retainer web sections and with one connection web section connecting the retainer web sections, wherein the free ends of the at least two retainer web sections can be at least partially fixed in a respective one of the two repositioned bone fragments. Advantageously the clip-like implant has a C-shaped cross section, in which the first and second retainer web sections each enclose with the connection web section an angle (w, w') between 75° and 90°, and the free ends of the at least two retainer web sections are designed as inwardly directed points.

19 Claims, 3 Drawing Sheets

FOREIGN PATENT DOCUMENTS

| | | |
|---|---|---|
| EP | 752238 | 1/1997 |
| EP | 826340 | 3/1998 |
| EP | 893104 | 1/1999 |
| EP | 0 488 906 | 6/1999 |
| WO | WO8300010 | 1/1983 |
| WO | WO9217122 | 10/1992 |
| WO | WO 00/64360 | 11/2000 |
| WO | WO0209592 | 2/2002 |
| WO | WO0219888 | 3/2002 |

* cited by examiner

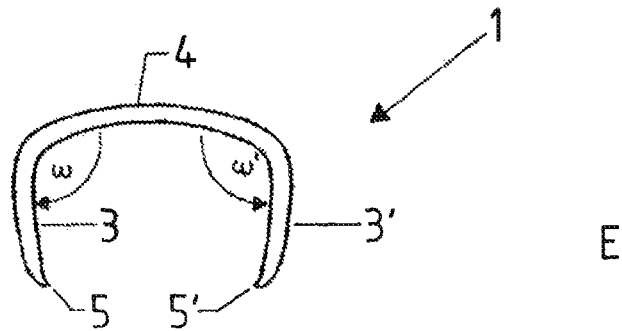
FIG. 1
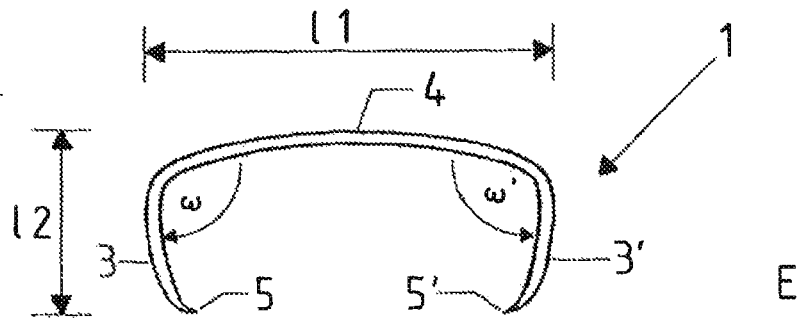
FIG. 2
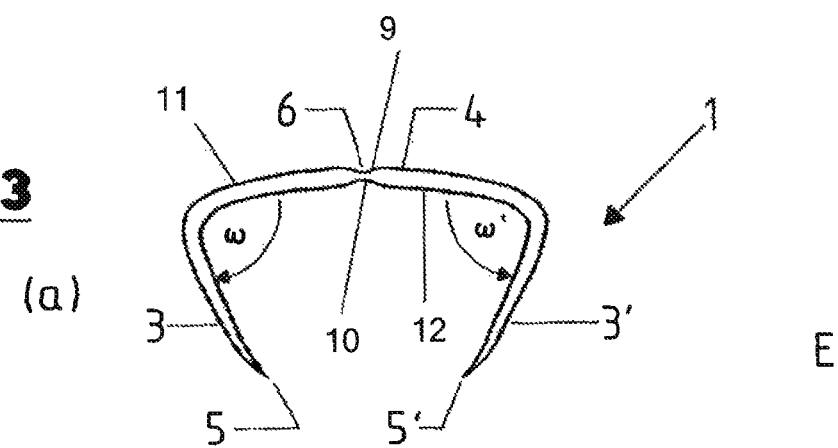
FIG. 3 (a)
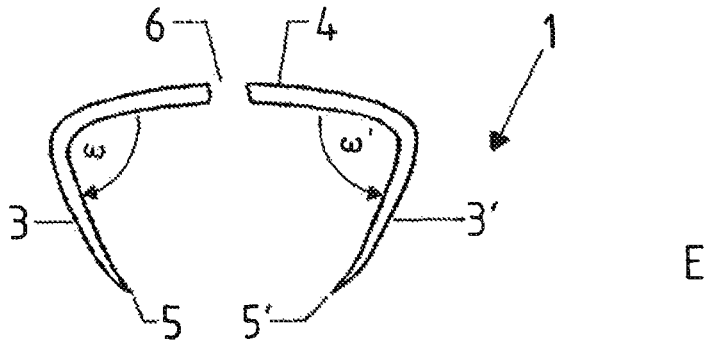
(b)

CLIP-LIKE IMPLANT FOR OSTEOSYNTHESIS

BACKGROUND OF THE INVENTION

The invention relates to a clip-like implant for osteosynthesis of at least two repositioned bone fragments.

Clip-like implants for the surgical joining of repositioned bone fragments ("osteosynthesis") are known in the art, for example from US 2003/0139746 and U.S. Pat. No. 5,053,038, which can be used to stabilize at least two repositioned bone fragments in the anatomically correct position, in particular within the framework of osteosynthesis performed subsequent to surgical sectioning of bone ("osteotomy").

The disadvantage of such clip-like implants is that they do not provide sufficient fixing of the repositioned bone fragments for treatment of complicated first and second degree bone fractures, especially in the case of dynamic stress on the fixed bone fragments.

It is an object of the invention is to present a clip-like implant for osteosynthesis by means of which at least two repositioned bone fragments can be sufficiently fixed or stabilized easily and quickly with the least possible impact on the patient.

SUMMARY OF THE INVENTION

The essential aspects of the clip-like implant for osteosynthesis according to the invention are that the clip-like implant has a C-shaped cross section, the first and second retainer web section enclose with the respective connection web section an angle between 75° and 90° and the free ends of the at least two retainer web sections are designed as inwardly directed points. Advantageously, the clip-like implant can be fixed in the respective bone fragment by means of simple surgical instruments, in particular by driving the free ends of the at least two retainer web sections designed as points into the two opposing bone fragments, to stabilize the latter after repositioning. Due to the significantly reduced dimensions of the clip-like implant as compared with conventional plate implants, several implants can be surgically inserted via one small surgical opening, for example, thus also enabling treatment of large-surface fractures. The clip-like implants according to the invention can be manufactured inexpensively and can be driven into the bone fragments to be stabilized using a considerably simplified surgical procedure. Especially advantageously, the stability of the fixation is increased by the fact that due to the C-shaped design of the clip-like implant according to the invention, the inwardly directed points at least partially grip behind the bone wall.

BRIEF DESCRIPTION OF THE DRAWINGS

The invention is described below in more detail based on exemplary embodiments with reference to the drawings, as follows:

FIG. 1 is a simplified view of the clip-like implant according to the invention;

FIG. 2 is a simplified view of an alternative embodiment of a clip-like implant according to the invention;

FIG. 3a, b is a simplified view of a clip-like implant prior to and following its use for stabilizing the bone fragments;

DETAILED DESCRIPTION OF THE INVENTION

Figure 6:
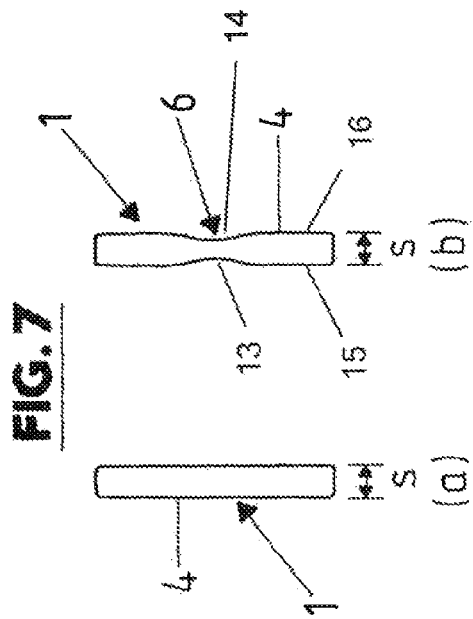
FIG. 6a is cross section through a bone fragment with an inserted clip-like implant.

In the drawings, 1 generally designates the clip-like implant according to the invention, which is intended for osteosynthesis of at least two repositioned bone fragments 2, 2', i.e. bone fragments that have been moved into the correct anatomical position.

The implant 1 preferably has a C-shaped cross section and comprises at least one first and second retainer web section 3, 3' and at least one connection web section 4 of a different thickness S (see FIGS. 1, 2, 3 and 8) connecting the two retainer web sections 3, 3'.

The connection web section 4 is preferably straight or rod-shaped or slightly curved and merges at its two ends into the first and second retainer web section 3, 3' with an form-fit. The two retainer web sections 3, 3' each stick out in the same direction from the connecting web section 4 and each have a point 5, 5' on their free ends. The first and second retainer web sections 3, 3' each enclose with the connection web section 4 in the plane E an angle w, w', depending on the application between 75° and 110°, preferably between 75° and 90°.

In an alternative embodiment, the implant 1 is slightly curved inwardly on its free ends, namely along the plane E formed by the retainer web sections 3, 3' and the connection web section 4, i.e. the points 5, 5' point toward each other. A wide variety of materials with different respective hardnesses can be used for the manufacture of the implant 1. In particular, metals, metal alloys or plastics are used that are suitable for use inside the body. For example, titanium alloys (TAL64V) or CO-CR cast alloys (CO CRMO) frequently are used for this purpose.

The surface of the clip-like implant 1 can be smooth, for example, or can have perforations or lamellar elements at least on the retainer web sections 3, 3', in order to prevent accidental loosening of the retainer web section 3, 3' fixed in the first or second bone fragment 2, 2'.

The clip-like implant 1 can be of a different size depending on the application, for example depending on the bone types to be fixed, such as hand bones or foot bones. In particular, the length l1 of the connection web section 4 can vary between 10 and 50 mm, for example. Also, the length l2 of the retainer web section 3, 3' can vary between 2 and 20 mm, for example. In an especially advantageous embodiment, the length l2 of the retainer web sections 3, 3' is adapted to the respective wall thickness or thickness of the bone wall 7 of the bone fragments 2, 2' to be fixed or is selected based on this thickness.

Further, the cross section of the clip-like implant 1 is, for example, square, rectangular, round, oval, triangular or trapezoidal or alternating sectionwise. The diameter or the thickness S of the material, in particular wire material, used for the manufacture of the clip-like implant 1, in a preferred embodiment is likewise selected based on the dimensions of the bone fragments 2, 2' to be fixed.

In particular, the surgical opening required for insertion of a clip-like implant 1, due to its comparatively short length l1, l2, is reduced significantly as compared with conventional plate implants. This enables the treatment of bone fractures by means of minimal invasive surgical procedures. Only a small incision in the skin of ca. 2-5 cm above the fracture is required for this procedure. Using a single-pronged hook for the repositioning, for example, the bone fragments 2, 2' are carefully brought together and then stabilized by means of the clip-like implant 1 according to the invention.

Figure 7:
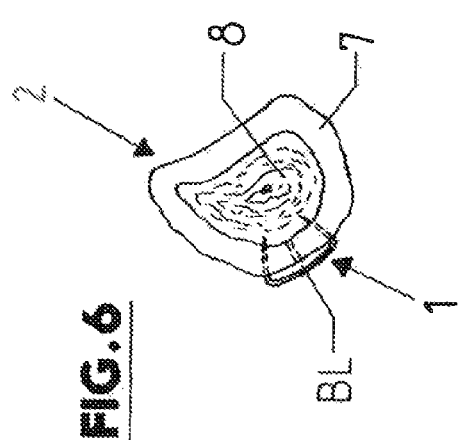
FIG. 7a, b is a simplified top view of the clip-like implants according to FIGS. 1 and 3.

In an alternative embodiment, and with reference to FIGS. 3(a) and 7(b), the connection web section 4 can feature at least one perforation or break line 6, which preferably is located in the area of half the length I1 of the connection web section 4, i.e. approximately midway. The perforation or break line 6 facilitates the separation of the clip-like implant 1 fixed in the bone fragments 2, 2' following the therapy of the bone fracture. The parts of the clip-like implant 1 inserted into the repositioned bone fragments 2 and now separated can easily be removed after being separated. The connection web section 4 of the clip-like implant 1 can, for example, be separated by means of a tong-like surgical instrument along the perforation or break line 6 and the remaining sections of the implant 1 can be removed through a minimal invasive surgical opening. The break line 6 of the connection web section 4 is a portion of the connection web section 4 having a smaller cross sectional area when viewed along a plane perpendicular to a longitudinal axis of the connector web section 4. The smaller cross sectional area of the connection web section 4 at the break line 6 is defined by a top and bottom recesses 9, 10 formed along the top and bottom walls 11, 12 of the connection web section 4 and first and second lateral recesses 13, 14 formed along the opposed lateral sides 15, 16 of the connection web section 4.

Figure 5:
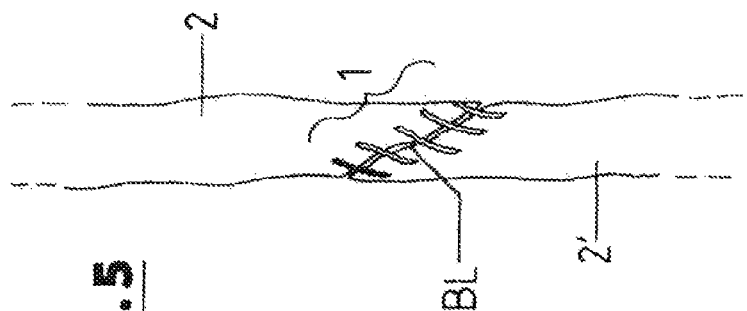
FIG. 5 is a schematic side view of a further bone fracture fixed by means of an array of several clip-like implants according to the invention.
Figure 4:
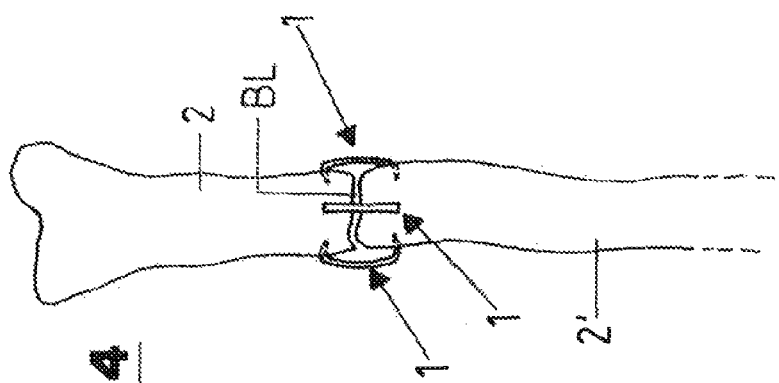
FIG. 4 is a schematic side view of two bone fragments fixed by means of the implant according to the invention.
Figure 8:
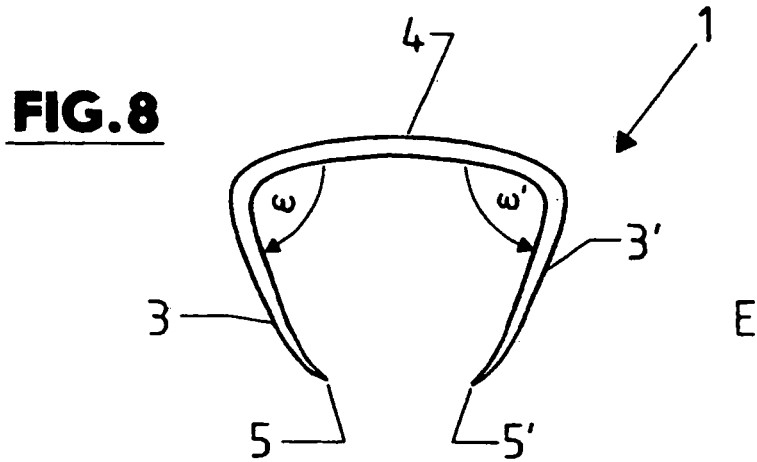
FIG. 8 is a simplified view of a further alternative embodiment of a clip-like implant according to the invention.
Figure 10:
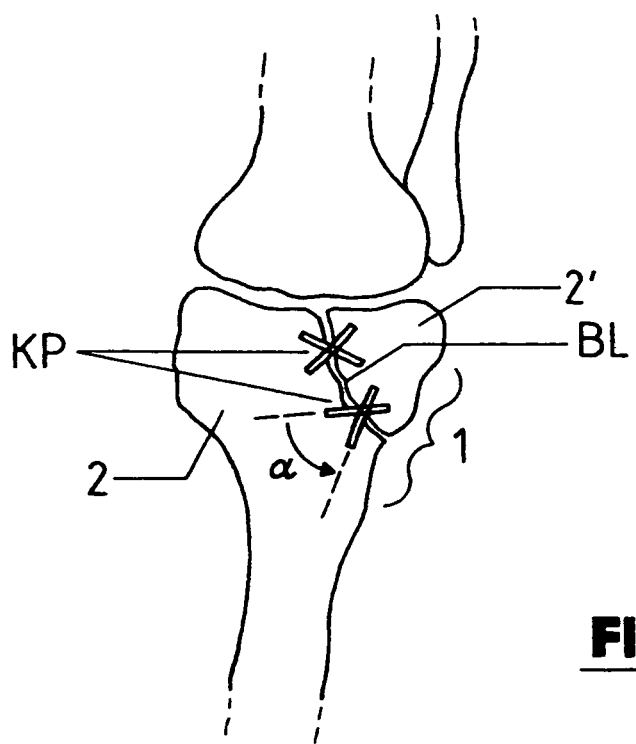
FIG. 10 is an arrangement of at least two C-shaped clip-like implants for fixing at least two bone fragments.

As depicted in FIGS. 4, 5 and 10, the implant 1 is driven respectively with the free ends or points 5, 5' of the at least two retainer web sections 3, 3' into the opposing repositioned bone fragments 2, 2', namely so that for example the straight connection web section 4 extends approximately perpendicular to the fracture line BL. In a particularly advantageous embodiment at least two implants 1 are inserted into the respectively opposing repositioned bone fragments 2, 2', so that the implants cross each other and the point of intersection KP lies above the fracture line BL. This produces an especially stable fixing of the at least two repositioned bone fragments 2, 2'. The angle α enclosed by the connection web sections 4 of the at least two crossed implants 1 is for example between 30° and 90°, preferably between 35° and 65°.

A mechanical or electrical device is used to insert the clip-like implant 1, in particular a "staple unit" or a "clip device" or a combination of a drill and one of the said devices, by means of which for example several implants 1 provided in a magazine are inserted by impact or thrust force generated by the device into the bone fragments 2, 2' to be joined. The surgeon therefore "clips" or "staples" the repositioned bone fragments 2, 2' by means of the device, i.e. the stapler or clip device.

The above-mentioned additional drilling functions can be used to make bore or guide holes at the connection locations in the bone fragments 2, 2' before insertion of the implant 1, said holes being provided for holding the two retainer web sections 3, 3' in the bone fragments 2, 2'. The clip-like implant 1 is inserted in a guided manner, so to speak, by means of the bore or guide holes. This virtually eliminates the possibility of the retainer web sections 3, 3' from breaking out or bending while they are being driven into the bone fragments 2, 2'. Before inserting the retainer web elements 3, 3' it is also possible to insert so-called tubular rivets or anchor elements into the bore or guide holes, for improved fixing of the clip-like implant 1 in the bone elements 2 and therefore for better holding of the retainer web sections 3, 3' of the implant 1 in the respective bone fragment 2, 2'.

In an alternative embodiment, at least the retainer web elements 2, 2' are designed as tubular rivets, which are used in bore holes, for example by means of known riveting methods.

The type of fastening depends on the dimensions or type of the bone fragments and of their wall thicknesses 7.

Figure 9:
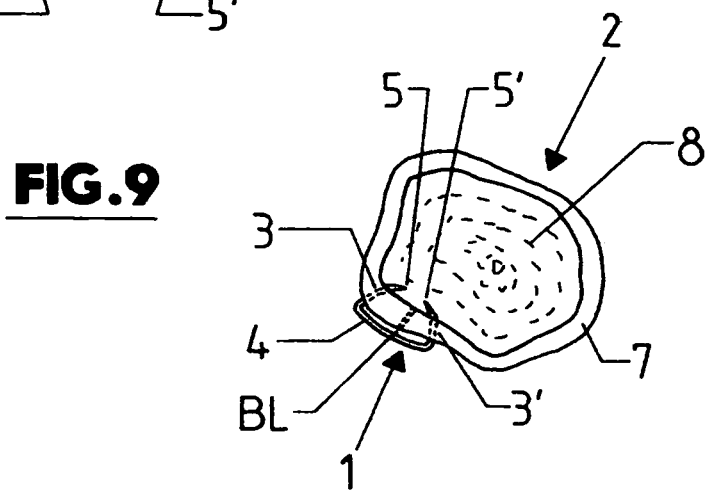
FIG. 9 is a further cross section through a bone fragment with an inserted C-shaped clip-like implant.

FIGS. 6 and 9 depict a section through a bone fragment 2, which shows the bone marrow 8 surrounded by a bone wall 7. The clip-like implant 1 driven into the bone fragment 2 adapts here to the surface of the bone fragment 2 or of the bone wall 7, i.e. the connection web section 4 extends either on or parallel to the surface of the bone wall 7. The two retainer web sections 3, 3' penetrate for example the bone wall 7 completely to the bone marrow 8 and at least partially grip behind the bone wall 7. Due to the C-shaped design of the clip-like implant 1 according to the invention, the inward directed points 5 of the clip-like implant 1 can therefore at least partially grip behind the bone wall 7 after insertion into the bone fragment 2, which additionally increases the stability of the fixation.

Therefore, the described clip-like implant 1 can be used effectively for osteosynthesis of at least two repositioned bone fragments 2, 2' in the case of bone fractures with different degrees of fracture, for example degree 1 through 3. Diverse types of bone fractures, for example also comminuted fractures and splintered fractures, can be fixed without plates, nails and/or wire.

To stabilize broad fracture lines BL or fracture areas, several such clip-like implants 1 can be used next to or following one another, or also crossed as depicted in FIG. 10. Many variations are conceivable, depending on the course of the fracture line(s) to be stabilized.

Advantageously, the use of such clip-like implants 1 has an extremely low impact on the patient, since a short anesthesia period is sufficient, due to the small dimensions of the surgical openings and the short duration of the surgery. The use of the implant 1 can therefore be carried out with low use of personnel and at extremely low costs, and also without cost-intensive special surgical instruments.

The invention was described above based on an exemplary embodiment. It goes without saying that numerous modifications or variations are possible without abandoning the underlying inventive idea upon which the invention is based.

For example, it is also possible to leave the clip-like implant 1 in the bone following the therapy of the bone fracture, due to its small dimensions.

REFERENCE TERMS 1 implant, clip-like
2, 2' bone fragments
3, 3' retainer web sections
4 connection web section
5, 5' points or free ends
6 perforation or break line
7 bone wall
8 bone marrow
BL fracture line or fracture area
E plane
I1 length of the connection web section
I2 length of the retainer web section
KP point of intersection
S thickness of the connection web section or implant
w, w' angle
α angle

What is claimed is:

1. A surgical clip-like implant for osteosynthesis of at least two repositioned bone fragments comprising first and second retainer web sections and with one connection web section connecting the first and second retainer web sections, the connection web section comprising a break line facilitating separation of the surgical clip-like implant fixed in the bone fragments as the separated surgical clip-like implant may be easily removed, the break line being composed of a portion of smaller cross sectional area formed along the connection web section when viewed along a plane perpendicular to a longitudinal axis of the connection web section, the break line including first and second lateral recesses formed along opposed lateral sides of the connection web section and top and bottom recesses formed along top and bottom walls of the connection web section defining the portion of smaller cross sectional area, wherein free ends of the first and second retainer web sections can be at least partially fixed in a respective one of the two repositioned bone fragments wherein the surgical clip-like implant has a C-shaped cross section and is manufactured of a wire material, the first and second retainer web sections each enclose with the connection web section an angle between 75° and 90°, and that the free ends of the first and second retainer web sections are inwardly directed points.

2. The surgical clip-like implant according to claim 1 wherein, the connection web section is slightly curved.

3. The surgical clip-like implant according to claim 1, wherein the connection web section merges on its two ends into the first and second retainer web section.

4. The surgical clip-like implant according to claim 1, wherein a length of the connection web section is selected based on dimensions of the bone fragments to be fixed.

5. The surgical clip-like implant according to claim 1, wherein a length of the first and second retainer web sections is selected based on dimensions of the bone fragments to be fixed or based on a thickness of the bone wall of the bone fragments to be fixed.

6. The surgical clip-like implant according to claim 1, wherein the surgical clip-like implant is comprised of a body-compatible metal, a metal alloy, a plastic or a combination thereof.

7. The surgical clip-like implant according to claim 1, wherein a thickness of the material used for manufacture of the surgical clip-like implant is selected based on the dimensions of the bone fragments to be fixed or based on a thickness of the bone wall of the bone fragments to be fixed.

8. The surgical clip-like implant according to claim 1, wherein the surgical clip-like implant is driven with the free ends of the first and second retainer web sections into the opposing repositioned bone fragments so that the connection web section extends approximately perpendicular to the fracture line.

9. The surgical clip-like implant according to claim 1, wherein the surgical clip-like implant is used for minimal invasive surgical procedures.

10. The surgical clip-like implant according to claim 1, wherein the surgical clip like implant is adapted to a surface of the bone fragment or a surface of the bone wall.

11. The surgical clip-like implant according to claim 1, wherein the first and second retainer web sections are retaining rivets, which can be inserted into bore holes provided in the hone fragment.

12. An arrangement for osteosynthesis of at least two repositioned bone fragments comprising at least two surgical clip-like implants as claimed in claim 1, wherein the at least two surgical clip-like implants are driven into respectively opposing repositioned bone fragments so that the surgical clip-like implants cross each other.

13. The arrangement according to claim 12, wherein the connection web sections of the at least two surgical clip-like implants enclose an angle ($\alpha$) between 30° and 90°.

14. An arrangement for driving in at least one surgical clip-like implant, as claimed in claim 1, into at least two repositioned bone fragments with the free ends of the first and second retainer web sections of the surgical clip-like implant ahead into the at least two repositioned bone fragment to be stabilized, the arrangement also including a staple unit wherein the staple unit additionally comprises a drilling function for creating bore and guide holes in the at least two repositioned bone fragments.

15. The arrangement according to claim 14, further comprising a magazine unit for holding several surgical clip-like implants.

16. A surgical clip-like implant for osteosynthesis of at least two repositioned bone fragments comprising first and second retainer web sections and with one connection web section connecting the first and second retainer web sections wherein free ends of the first and second retainer web sections can be at least partially fixed in a respective one of the two repositioned bone fragments wherein the surgical clip-like implant has a C-shaped cross section, the first and second retainer web sections each enclose with the connection web section art angle between 75° and 90°, and that the free ends of the first and second retainer web sections are inwardly directed points, and wherein the connection web section comprises a break line facilitating separation of the surgical clip-like implant fixed in the bone fragments as the separated surgical clip-like implant may be easily removed, the break line being composed of a portion of smaller cross sectional area formed along the connection web section when viewed along a plane perpendicular to a longitudinal axis of the connection web section, the break line including first and second lateral recesses formed along opposed lateral sides of the connection web section and top and bottom recesses formed along top and bottom walls of the connection web section defining the portion of smaller cross sectional area.

17. The surgical clip-like implant according to claim 16, wherein the connection web section is slightly curved.

18. The surgical clip like implant according to claim 16 wherein a length of the first and second retainer web sections is selected based on dimensions of the bone fragments to be fixed or based on a thickness of the bone wall of the bone fragments to be fixed.

19. The surgical clip-like implant according to claim 16, wherein the surgical clip-like implant is comprised of a body-compatible metal, a metal alloy, a plastic or a combination thereof.

* * * * *

UNITED STATES PATENT AND TRADEMARK OFFICE
CERTIFICATE OF CORRECTION

PATENT NO. : 8,475,457 B2
APPLICATION NO. : 12/223713
DATED : July 2, 2013
INVENTOR(S) : Majid Shano It is certified that error appears in the above-identified patent and that said Letters Patent is hereby corrected as shown below:

In the Claims:

Column 5, lines 26-27, cancel the text beginning with "2. The surgical clip-like" to and ending "is slightly curved.", and insert the following claim:

-- 2. The surgical clip-like implant according to claim 1, wherein the connection web section is slightly curved. --

Column 5, lines 57-59, cancel the text beginning with "10. The surgical clip-like" to and ending "of the bone wall.", and insert the following claim:

-- 10. The surgical clip-like implant according to claim 1, wherein the surgical clip-like implant is adapted to a surface of the bone fragment or a surface of the bone wall. --

Column 6, lines 51-55, cancel the text beginning with "18. The surgical clip like" to and ending with "to be fixed.", and insert the following claim:

-- 18. The surgical clip-like implant according to claim 16 wherein a length of the first and second retainer web sections is selected based on dimensions of the bone fragments to be fixed or based on a thickness of the bone wall of the bone fragments to be fixed. --

Signed and Sealed this
Twenty-second Day of October, 2013

Teresa Stanek Rea
*Deputy Director of the United States Patent and Trademark Office*